United States Patent [19]

Günther et al.

[11] Patent Number: 4,590,167
[45] Date of Patent: May 20, 1986

[54] THIN-LAYER CHROMATOGRAPHIC METHOD FOR THE SEPARATION OF ENANTIOMERS

[75] Inventors: Kurt Günther, Erlensee; Jürgen Martens, Alzenau; Maren Schickedanz, Dietzenbach, all of Fed. Rep. of Germany

[73] Assignee: Degussa Aktiengesellschaft, Frankfurt am Main, Fed. Rep. of Germany

[21] Appl. No.: 634,685

[22] Filed: Jul. 25, 1984

[30] Foreign Application Priority Data

Aug. 5, 1983 [DE] Fed. Rep. of Germany ....... 3328348

[51] Int. Cl.$^4$ ............................................... B01D 15/08
[52] U.S. Cl. ..................................... 436/162; 210/658
[58] Field of Search ................... 210/658, 198.2, 198.3; 436/162

[56] References Cited

U.S. PATENT DOCUMENTS

| 3,647,684 | 3/1972 | Malcomb ............................ | 210/658 |
| 4,415,631 | 11/1983 | Schutijser ............................ | 210/656 |
| 4,431,546 | 2/1984 | Hughes et al. ....................... | 210/656 |
| 4,469,875 | 9/1984 | Busker et al. ....................... | 210/656 |

OTHER PUBLICATIONS

Ligand Chromatography and the Preparation of Optically Active Compounds by Davankov Soviet Science Review, vol. 3, No. 6, Nov. 1972, pp. 352–356.

Resolution of the Optical Isomers of Dansyl Amino Acids by Reverse Phase Liquid Chromatography with Optically Active Metal Chelate Additives by Page et al., Analytical Chemistry, vol. 51, No. 3, Mar. 1979, pp. 433–435.

Primary Examiner—John Adee
Attorney, Agent, or Firm—Cooper, Dunham, Clark, Griffin & Moran

[57] ABSTRACT

Thin-layer chromatography is employed to separate enantiomers of the general formula,

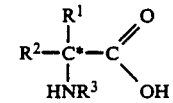

in which C* represents an asymmetric center and the substituents $R^1$, $R^2$, and $R^3$ are such that they supply the structural element

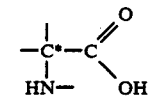

for α-amino- or α-iminocarboxylic acids, particularly the well-known α-amino- or α-iminocarboxylic or for derivatives of such carboxylic acids, either of which contains no free thiol groups. In the thin-layer chromatographic separation operation a TLC plate is used which is coated with silica gel hydrophobicized by a silane derivative and which is further impregnated with an ionic compound of a divalent transition metal and a chiral selector. The mobile phase employed is a ternary mixture of a water-miscible alkanol, such as methanol, water, and acetonitrile, or a quaternary mixture of the latter ternary mixture to which a water-miscible cyclic ether, such as tetrahydrofuran, has been added.

5 Claims, No Drawings

THIN-LAYER CHROMATOGRAPHIC METHOD FOR THE SEPARATION OF ENANTIOMERS

BACKGROUND OF THE INVENTION

This invention is directed to a method for the thin-layer chromatographic separation of enantiomers of the general formula

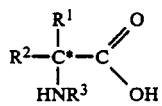

in which C* represents an asymmetry center and the substituents $R^1$, $R^2$, and $R^3$ are such that they provide the structural element

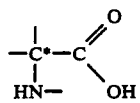

for α-amino- or α-iminocarboxylic acids or for a derivative of such carboxylic acids, either of which contains no free thiol groups, by means of ligand exchange to a chiral stationary phase.

It is known that enantiomers can be separated by high-pressure liquid chromatography (HPLC) on a chiral stationary phase and the preferred method is the ligand exchange chromatography method as reviewed by W. Lindner [Chimia, 35, 294 (1981)]. However, these HPLC separation methods have the disadvantage of requiring relatively expensive and troublesome apparatus as well as considerable time to prepare and execute the separation. They are therefore less suitable for routine analysis and especially for process control.

It is an object of this invention to provide a simplified method for the separation of enantiomers of the general formula (I) and in particular to provide a simple method that can be carried out quickly and is suitable for process or plant control, for example, purity assays.

SUMMARY OF THE INVENTION

Thin-layer chromatography is employed to separate enantiomers of the general formula,

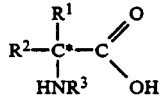

in which C* represents an asymmetric center and the substituents $R^1$, $R^2$, and $R^3$ are such that they supply the structural element,

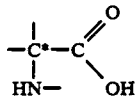

for α-amino- or α-iminocarboxylic acids, particularly the well-known α-amino- or α-iminocarboxylic acids or for derivatives of such carboxylic acids, either of which contains no free thiol groups. In the thin-layer chromatographic separation operation a TLC plate is used which is coated with silica gel hydrophobicized by a silane derivative and which is further impregnated with an ionic compound of a divalent transition metal and a chiral selector. The mobile phase employed is a ternary mixture of water-miscible alkanol, such as methanol, water, and acetonitrile, or a quaternary mixture of the latter ternary mixture to which a water-miscible cyclic ether, such as tetrahydrofuran, has been added.

DETAILED DESCRIPTION OF THE INVENTION

The chiral stationary phase for the thin-layer chromatography (TLC) employed in the practices of this invention is any of the well-known TLC plates coated with hydrophobicized silica gel. Such plates, made of glass or a suitable foil, are readily commercially available as so-called reversephase plates wherein the silica gel has already been made hydrophobic by the manufacturer with a chemical compound or by physical adsorption of a hydrophobic material. Reversephase plates that are particularly suitable are such plates as Types RP 2, RP 8, RP 12, and especially RP 18. The numbers in this designations represent the alkane silane derivative with which the silica gel has been hydrophobicized: methyl(2), octyl-(8), dodecyl-(12), and octadecylsilane derivative-(18). Examples of silane derivatives that are suitable for hydrophobicization are the corresponding trichlorosilanes, dichloromethylsilanes, or dimethoxymethylsilanes.

The TLC plates to be used must also be impregnated with an ionic compound of a divalent transition metal and a chiral selector.

Suitable transition-metal compounds are those that contain such ions as $Ni^{++}$, $Zn^{++}$, $Cd^{++}$, $Hg^{++}$, $Co^{++}$, or especially $Cu^{++}$.

Suitable chiral selectors are essentially all the compounds customarily employed for HPLC ligand-exchange chromatography, for example, N-heptyl-L-hydroxyproline, N-decyl-L-hydroxyproline, N-hexadecyl-L-hydroxyproline, or the chiral selectors named in [chimia, 35,294–307 (1981)].

Chiral selectors that are especially preferred in the practices of this invention are the optically active proline derivatives with the general formula,

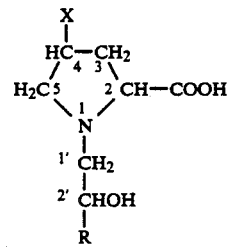

in which X denotes hydrogen or a hydroxyl group and R denotes an unsubstituted phenyl residue or a phenyl residue substituted with lower alkyl groups or a straight-chain or branched alkyl residue with 1 to 20 carbon atoms, preferably 6 to 16 carbon atoms, in particular 10 to 12 carbon atoms. All the proline derivatives with the general formula (II) are sterically uniform with respect to the asymmetric carbon atom in position 2, and also with respect to the asymmetric carbon in position 4 when X=OH. By contrast, the absolute configuration of the asymmetric carbon atom in the 2' position on the side chain must not be uniform. This means that a proline derivative with the general formula (II)

can also be introduced as a mixture of two diastereomers. The proline derivatives of the general formula (II) and a method for their preparation from optically pure proline or 4-hydroxyproline and the corresponding epoxides are described in detail in DE-OS No. 31 53 726.

The TLC plates to be used are coated with silica gel hydrophobicized by a silane derivative and additionally impregnated with an ionic compound of a divalent transition metal and a chiral selector and are prepared by the following method:

Start with one of the commercial reverse-phase plates mentioned above. Immerse the plate in a solution of a suitable transition-metal compound, for example copper (II) acetate, in a mixture of 1 part by volume of methanol and 9 parts by volume of water. Appropriate concentrations of the transition-metal compound in this solution are in the range about 0.01–1.0 weight percent, preferably between about 0.1 and about 0.5 weight percent. One minute of immersion time is generally completely sufficient. Allow the plate to drain for a short time and dry at a temperature between 90° and 150° C., preferably between 100° and 120° C. Then immerse the plate in a methanol solution of the chiral selector. Appropriate selector concentrations in this solution lie between about 0.1 and about 2.5 weight percent, preferably between about 0.5 and about 1.5 weight percent, especially between 0.7 and 1.1 weight percent. A one-minute immersion is again completely sufficient. Again let the plate drain for a short time and dry it in air at a temperature between 20° and 30° C. A plate prepared in this manner is usable immediately for the subject method of the invention and is stable for several months of storage.

Alternatively, suitable TLC plates can be prepared by mixing a paste of hydrophobic silica gel prepared as described in the JOURNAL OF CHROMATOGRAPHY, 154, 68 (1978), for example, in a mixture of ethanol and water with the ionic compound of a divalent transition metal and the chiral selector. After adding a binding agent, such as calcium sulfate, for example, coat a glass support plate or a suitable foil with the paste.

To perform the separation, apply to the starting point in the customary manner about 2 µl of a solution of about 1 weight percent of the sample to be tested and develop in the usual way with a suitable mobile phase in a TLC chamber.

Suitable mobile phases for the subject method of the invention are ternary mixtures of a water-miscible alkanol, water, and acetonitrile, or quaternary mixtures that contain a water-miscible cyclic ether in addition to the components mentioned. Suitable alkanols are methanol, ethanol, propane-1-ol, and propane-2-ol, of which methanol is preferable 1,4-dioxane and especially tetrahydrofuran are preferable as the cyclic ether. The appropriate compositions of the ternary mixture fall between about 25 and about 75 parts by volume of the alkanol, about 25 to about 75 parts by volume of water, and about 100 to about 300 parts by volume of acetonitrile, and for the quaternary mixture between about 30 and about 70 parts by volume of the alkanol, about 30 to about 70 parts by volume of water, about 100 to about 150 parts by volume of acetonitrile, and about 50 to about 100 parts by volume of the cyclic ether.

The developed plate is removed from the TLC chamber and dried by air drying, such as with the aid of a hair dryer or in some other manner customary in TLC practice. The spots assigned to the (R)-enantiomer and the (S)-enantiomer, already partly visible in UV light, can be made clearly visible by spraying with a ninhydrin solution or another suitable spraying reagent, for example, solutions of sulfuric acid or iodine.

If a standardized mixture of both enantiomers to be separated is applied to the TLC plate parallel to the test sample, it is possible to make a semiquantitative determination of the test sample composition by visually comparing the sizes of the spots. In this way, for example, one can detect somewhat more than 1 weight percent of a D-aminocarboxylic acid in an L-aminocarboxylcic acid that is beginning to racemize.

Enantiomers of the general formula (I) can be separated in a simple manner by employing this invention. The method of this invention is particularly suitable for those compounds of the general formula (I) in which hydrogen is either the substituent $R^1$ or the substituent $R^2$. It is an especially suitable for the separation of phenylalanine enantiomers and for those derivatives in which the substituent is attached to the phenyl ring of the compound, tryptophan and its derivatives, tyrosine and O-substituted tyrosines, proline, isoleucine, norleucine, glutamine, 3-thiazolidine-4-carboxylic acid, and those derivatives of the latter compound in which the substituent is in position 5, S-substituted cystein derivatives and 0-substituted serine derivatives. 3-cyclopentylalanine is another example of a compound whose enantiomers can be separated by the subject method.

The invention is exemplified in more detail by the following examples. The percentages given are weight percentages in all instances.

EXAMPLE 1

A commercial TLC plate coated with silica gel made hydrophobic by an octadecylsilane derivative was set in place. The plate was immersed for one minute in a solution of 0.25% copper (II) acetate in a mixture of 1 part by volume of methanol and 9 parts by volume of water, allowed to drain for a short time, and dried at 110° C. The plate thus impregnated with copper (II) acetate was then immersed for one minute in a 0.8% methanol solution of (2S, 4R, 2'RS)-N-(2'-hydroxy-dodecyl)-4-hydroxyproline, allowed to drain for a short time, and allowed to dry in air at room temperature.

A 1% solution of a phenylalanine of unknown enantiomer composition was prepared in a methanol-water mixture of the same volumetric composition as the sample to be tested for the purpose of comparing the respective solutions of racemic (RS)-phenylalanine with the pure (R)- and the pure (S)-phenylalanine.

A 2-µl portion of each of these solutions was applied to the prepared TLC plate and developed with a mobile phase of methanol, water, and acetonitrile in a 1:1:4 ratio by volume.

When the mobile phase front had attained a height of 14 cm after 30 minutes, the solvent mixture was allowed to evaporate and the plate was sprayed with a commercial 0.1% ninhydrin solution and dried for 30 minutes at 120° C.

The racemic (RS) phenylalanine gave two large violet spots of equal size clearly separated from each other with $R_f$-values of 0.38 and 0.45; the pure (R)-phenylaline gave a single spot with an $R_f$-value of 0.38; and the pure (S)-phenylalanine gave a single spot with an $R_f$-value of 0.45. The sample under test gave two spots of different size with $R_f$-values of 0.38 and 0.45. The latter sample is accordingly a partly racemized phenylaline.

EXAMPLE 2

Example 1 was repeated with the only difference being the mobile phase was a mixture of ethanol, water, and acetonitrile in a 1:1:4 ratio by volume. In this case, the (R)-phenylalanine gave a spot with an $R_f$-value of 0.37 and the (S)-phenylalanine again gave a spot with an $R_f$-value of 0.45.

EXAMPLE 3

Example 1 was repeated with the only difference being the mobile phase was a mixture of propane-2-ol, water, and acetonitrile in a 1:1:4 ratio by volume. In this case, the (R)-phenylalanine gave a spot with an $R_f$-value of 0.37 and the (S)-phenylalanine gave a spot with an $R_f$-value of 0.45.

EXAMPLES 4 to 9

Various racemic phenylalanines substituted in position 4 were separated by means of the TLC plate prepared as described in Example 1 and the mobile phase used therein. The compounds used and the $R_f$-values obtained were as follows:

| Example | (RS)—Amino acid | $R_f$ Values |
|---|---|---|
| 4 | 4-chlorophenylalanine | 0.31 and 0.41 |
| 5 | 4-bromophenylalanine | 0.28 and 0.40 |
| 6 | 4-iodophenylalanine | 0.26 and 0.38 |
| 7 | 4-nitrophenylalanine | 0.41 and 0.48 |
| 8 | 4-methoxyphenylalanine | 0.38 and 0.46 |
| 9 | 3-bromophenylalanine | 0.32 and 0.41 |

EXAMPLE 10

Example 1 was repeated with the difference that the sample to be tested was a tryptophan of unknown enantiomer composition and the comparison samples were (RS)-, (R)-, and (S)-tryptophan. In this case, the (R)-tryptophan gave a spot with an $R_f$-value of 0.39 and the (S)-tryptophan gave a spot with an $R_f$-value of 0.45.

EXAMPLES 11 to 14

Various racemic substituted tryptophanes were separated by means of the TLC plate prepared as described in Example 1 and the mobile phase used therein. The compounds used and the $R_f$-values obtained were as follows:

| Example | (RS)—Amino acid | $R_f$ Values |
|---|---|---|
| 11 | 5-methyltryptophan | 0.36 and 0.43 |
| 12 | 6-methyltryptophan | 0.36 and 0.45 |
| 13 | 7-methyltryptophan | 0.35 and 0.44 |
| 14 | 5-methoxytryptophan | 0.41 and 0.48 |

EXAMPLE 15

Example 1 was repeated with the difference that the sample to be tested was a tyrosine of unknown enantiomer composition, the comparison samples were (RS)-, (R)-, and (S)-tyrosine, and the mobile phase was a mixture of methanol, water, and acetonitrile in a 1:1:0.6 ratio by volume. In this case, the (R)-tyrosine gave a spot with an $R_f$-value of 0.34 and the (S)-tyrosine gave a spot with an $R_f$ value of 0.26.

EXAMPLE 16

Racemic O-benzyltyrosine was separated by means of the TLC plate prepared as described in Example 1 and the mobile phase used therein. The $R_f$-values were 0.26 and 0.38.

EXAMPLE 17

Example 15 was repeated with the difference that the sample to be tested was a proline of unknown enantiomer composition and the comparison samples were (RS)-, (R)-, and (S)-proine. In this case, the (R)-proline gave a spot with an $R_f$-value of 0.40 and the (S)-proline gave a spot with an $R_f$-value of 0.59.

EXAMPLE 18

Example 1 was repeated with the difference that the sample to be tested was an isoleucine of unknown enantiomer composition and the comparison samples were (RS)-, (R)-, and (S)-isoleucine. All the samples were free of alloisoleucine. In this case, the (2S, 3S)-2-amino-3-methyl-n-valeric acid gave a spot with an $R_f$-value of 0.37.

EXAMPLE 19

Racemic norleucine was separated by means of the TLC plate prepared as described in Example 1 and the mobile phase used therein. The $R_f$-values were 0.33 and 0.42.

EXAMPLE 20

Example 1 was repeated with the difference that the sample to be tested was a glutamine of unknown enantiomer composition, the comparison samples were (RS)-, (R)-, and (S)-glutamine and the TLC plate employed was impregnated with (2S, 2'-RS)-N-(2'-hydroxytetradecyl)proline as the chiral selector instead of (2S, 4R, 2'RS)-N-(2'hydroxydodecyl)-4-hydroxyproline.

When the mobile phase front had reached a height of 14 cm after 40 minutes, the solvent mixture was allowed to evaporate and the plate was sprayed with a commercial 0.1% ninhydrin solution and dried 45 minutes at 115° C.

The racemic (RS)-glutamine gave two spots of equal size clearly separated from one another with $R_f$-values of 0.19 and 0.35; the pure (R)-glutamine gave a single spot with an $R_f$-value of 0.35; the pure (S)-glutamine gave a single spot with an $R_f$ value of 0.19 and the test sample gave two spots of different size with $R_f$ values of 0.19 and 0.35. The latter sample was shown to be a partly racemized glutamine.

EXAMPLE 21

The procedure was the same as in Example 20 with the difference that the TLC plate used was impregnated with (2R, 2'RS)-N-(2'hydroxytetradecyl)proline as the chiral selector instead of the (2S, 2'RS)-form. In this case, the (R)-glutamine gave a spot with an $R_f$-value of 0.19 and the (S)-glutamine gave a spot with an $R_f$-value of 0.35. The $R_f$-values found were thus exactly the reverse of those of Example 20.

EXAMPLE 22

The procedure was the same as in Example 20 with the difference that the TLC plate used was impregnated with (2S, 2'-RS)-N-(2'-hydroxyhexadecyl)proline as the chiral selector instead of (2S, 2'RS)-N-(2'-hydroxytetradecyl)proline. In this case, the (R)-glutamine gave a spot with an $R_f$-value of 0.34 and the (S)-glutamine gave a spot with an $R_f$-value of 0.19.

EXAMPLE 23

Example 1 was repeated with the difference that the sample to be tested was a glutamine of unknown enantiomer composition, the comparison samples were (RS)-, (R)-, and (S)-glutamine, and the mobile phase was a mixture of methanol, water, acetonitrile, and tetrahydrofuran in a 1:1:2:2 ratio by volume. In this case, the (R)-glutamine gave a spot with an $R_f$-value of 0.70 and the (S)-glutamine gave a spot with an $R_f$-value of 0.62.

EXAMPLE 24

In order to obtain a semiquantitative determination of (R)-glutamine in partly racemized (S)-glutamine by visual comparison of spot size, Example 1 was repeated with the difference that the sample to be tested was a partly racemized (S)-glutamine and the comparison (RS)-, (R)-, and (S)-glutamines were 1% glutamine solutions containing 10, 8, 5, 4, 3, 2 and 1% (R)-glutamine with (S)-glutamine making up the remainder in each instance. The (R)-glutamine gave a spot with an $R_f$-value of 0.53 and the (S)-glutamine gave a spot with an $R_f$-value of 0.37.

It could be estimated by visual comparison of the sizes of the spots with an $R_f$-value of 0.53 that the sample to be tested contained about 1% (R)-glutamine.

EXAMPLE 25

Example 1 was repeated with the difference that the sample to be tested was a 3-thiazolidine 4-carboxylic acid of unknown enantiomer composition and the comparison samples were (RS)-, (R)-, and (S)-3-thiazolidine-4-carboxylic acid. In this case, the (R)-enantiometer gave a spot with an $R_f$-value of 0.52 and the (S) enantiomer gave a spot with an $R_f$-value of 42.

This procedure may be employed, for example, to detect (S)-cystein in partly racemized (R)-cystein. Since the enantiomeric cysteins cannot be separated as such by the procedure specified in the invention, they are converted to the respective 3-thiazolidine-4-carboxylic acid derivatives.

For this purpose, partly racemized (R)-cystein was used as the sample to be tested and the comparison samples were (RS)-, (R)-, and (S)-cystein, 25 mg of each compound mixed with 25 mg of paraformaldehyde. The samples so mixed were dissolved in a mixture of 2.5 ml of propane-2-ol and 25 μl of concentrated hydrochloric acid and heated 2 hours at 60° C. After it had been cooled to 25° C., a 2- μl portion of each of the resulting reaction mixtures was applied directly to the TLC plate prepared as described in Example 1 and developed with the mobile phase employed in Example 1.

When the mobile phase front had attained a height of 14 cm after 45 minutes, the solvent mixture was allowed to evaporate and the plate was sprayed with the 0.1% ninhydrin solution and dried at 125° C. in a drying oven.

The (R)-cystein derivative gave a spot with an $R_f$-value of 0.52. The (S)-cystein derivative gave a spot with an $R_f$-value of 0.42.

EXAMPLE 26

Example 25 was repeated with the single difference that, instead of 3-thiazolidine-4-carboxylic acid, the corresponding 5,5-dimethyl-3-thiazolidine-4-carboxylic acid was used. In this case, the (R)-enantiomer gave a spot with an $R_f$-value of 0.50 and the (S)-enantiomer gave a spot with an $R_f$-value of 0.35.

This procedure may be employed, for example, to separate the enantiomers of penicillamine if a derivative of the latter compound is prepared by the method described in Example 25 for cystein to form the corresponding 5,5-dimethyl-3-thiazolidine-4-carboxylic acid and that compound is further treated as in Example 25. The (R)-penicillamine derivative then again gives a spot with an $R_f$-value of 0.50 and the (S)-penicillamine derivative gave a spot with an $R_f$-value of 0.35.

EXAMPLES 27 to 30

Various racemic S-substituted cysteins were separated by means of the TLC plate prepared as described in Example 1 and the mobile phase used therein. The compounds used and the $R_f$-values obtained were as follows:

| Example | (RS)—Cystein Derivative | $R_f$-Values |
|---|---|---|
| 27 | S—[(methylthiol)-methyl]cystein | 0.37 and 0.49 |
| 28 | S—[(2-(methylthiol)-ethyl]cystein | 0.35 and 0.48 |
| 29 | S—(2-chlorobenzyl)cystein | 0.27 and 0.39 |
| 30 | S—[2-(2'-pyridyl)-ethyl]cystein | 0.19 and 0.31 |

EXAMPLE 31

Racemic O-(benzyl)-serine was separated by means of the TLC plate prepared as described in Example 1 and the mobile phase used therein. The $R_f$-values for both enantiomers were 0.26 and 0.38.

EXAMPLE 32

Racemic 3-cyclopentylalanine was separated by means of the TLC plate prepared as described in Example 1 and the mobile phase employed therein. The $R_f$-values for both enantiomers were 0.29 and 0.38.

What is claimed is:

1. A method for the chromatographic separation of enantiomers of alpha-aminocarboxylic and alpha-iminocarboxylic acids of the general formula:

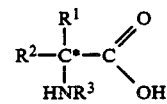

in which C* represents an asymmetry center and the substituents $R^1$, $R^2$ and $R^3$ are such that they provide the structural element,

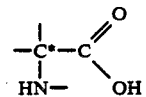

derivatives of said carboxylic acids, either of which contains no free thiol group, which comprises carrying out a thin layer chromatographic separation of said enantiomers on a chromatographic plate, including ligand exchange with a chiral stationary phase, said chromatographic plate being coated with silica gel made hydrophobic with a silane derivative and impregnated with an ionic compound of a divalent transition metal and a chiral selector and employing as the mobile phase in the chromatographic separation operation a ternary mixture containing water-miscible alkanol, water and acetonitrile or a quaternary mixture of a water-miscible alkanol, water, acetonitrile and a water-miscible cyclic ether.

2. A method in accordance with claim 1 wherein said chiral selector is an optically active proline derivative of the general formula,

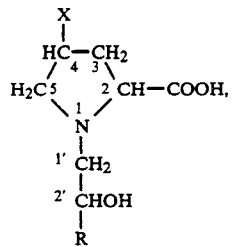 (II)

in which X denotes hydrogen or a hydroxyl group and R denotes an unsubstituted phenyl residue or a phenyl residue substituted with lower alkyl groups or a straight-chain or branched alkyl residue with 1 to 20 carbon atoms.

3. A method in accordance with claim 1 wherein said ionic compound is a $Cu^{++}$ compound.

4. A method in accordance with claim 1 wherein said water-miscible alkanol is methanol.

5. A method in accordance with claim 1 wherein said water-miscible ether is tetrahydrofuran.

* * * * *